United States Patent [19]

Berg

[11] Patent Number: 4,966,658

[45] Date of Patent: Oct. 30, 1990

[54] RECOVERY OF ETHYLENE GLYCOL FROM BUTANEDIOL ISOMERS BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 548,553

[22] Filed: Jul. 5, 1990

Related U.S. Application Data

[60] Continuation-in-part of Ser. No. 505,663, Apr. 5, 1990, abandoned, which is a division of Ser. No. 457,868, Dec. 27, 1989, Pat. No. 4,935,102.

[51] Int. Cl.$^5$ .......................... B01D 3/36; C07C 31/20
[52] U.S. Cl. ...................................... 203/62; 203/63; 203/69; 568/868
[58] Field of Search ............................ 203/62, 63, 69; 568/868

[56] References Cited

U.S. PATENT DOCUMENTS

| | | | |
|---|---|---|---|
| 3,859,368 | 1/1975 | Kollar | 568/868 |
| 4,057,471 | 11/1977 | Chueh | 568/868 |
| 4,151,048 | 4/1979 | Becker | 568/868 |
| 4,187,153 | 2/1980 | Peltzman | 568/868 |
| 4,276,126 | 6/1981 | Saffer | 568/868 |

*Primary Examiner*—Wilbur Bascomb

[57] ABSTRACT

Ethylene glycol cannot be easily separated from 1,2-butanediol or 1,3-butanediol by atmospheric or reduced pressure distillation because of the closeness of their boiling points. Ethylene glycol can be readily separated from the butanediols by azeotropic distillation. Typical effective agents are ethyl benzene, 3-heptanone or diisobutyl ketone.

2 Claims, No Drawings

4,966,658

RECOVERY OF ETHYLENE GLYCOL FROM BUTANEDIOL ISOMERS BY AZEOTROPIC DISTILLATION

This application is a continuation-in-part of application Ser. No. 07/505,663 filed 4-5-90, now abandoned, which is a division of application Ser. No. 07/457,868 filed 12-27-90, now U.S. Pat. No. 4,935,102.

FIELD OF THE INVENTION

This invention relates to a method for separating ethylene glycol from butanediol isomers using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

In the hydrocracking of higher carbohydrates such as glucose, sorbitol or sucrose, the molecule is broken into fragments of lower molecular weight to form compounds which belong to the glycol or polyol family. Some of the resulting polyols boil so close to one another that their separation by ordinary rectification is difficult. The relative volatility is so low that a large number of theoretical plates are required to produce high purity polyols.

Three of the close boiling glycols encountered in this process are 1,2-butanediol, b.p.=192° C., ethylene glycol, b.p.=198° C. and 1,3-butanediol, b.p.=206° C.

TABLE 1

| Plates Required To Effect Separation In 99% Purity | | |
|---|---|---|
| Relative Volatility | Theoretical Plates | Actual Plates 75% Efficiency |
| 1.10 | 97 | 129 |
| 1.25 | 41 | 55 |
| 1.35 | 31 | 42 |
| 1.45 | 25 | 34 |
| 1.50 | 23 | 31 |
| 1.70 | 18 | 24 |

The difficulty of separating these one from another by rectification can be shown by the data presented in Table 1. Table 1 shows that rectification of ethylene glycol from 1,2-butanediol, relative volatility of 1.25, in 99% purity requires 55 actual plates. Using azeotropic distillation with an agent yielding a relative volatility of 1.7 would require only 24 actual plates. Thus, azeotropic distillation would be an attractive method of effecting the separation of these two glycols if agents can be found that (1) will increase the relative volatility of ethylene glycol to 1,2-butanediol and 1,3-butanediol and (2) are easy to recover from the ethylene glycol.

Azeotropic distillation typically requires from one to five parts as much agent as ethylene glycol being boiled up in the column which increases the heat requirement as well as larger diameter plates to accommodate the increased liquid and vapor in the column.

The catalytic hydrocracking of sorbitol gave a mixture of polyols having the composition shown in Table 2. The principal products were

TABLE 2

| Polyols Produced By Hydrocracking Of Sorbitol | | |
|---|---|---|
| Compound | Weight Percent | Boiling Point, °C. |
| 2,3-Butanediol | 3.5 | 182 |
| Propylene glycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerine | 38.8 | 290 |
| 1,2,4-Butanetriol | 4.8 | 190/18 mm. |
| | 100.0 | |

16.5% propylene glycol, 25.2% ethylene glycol and 38.8% glycerine. To be of commercial value in most uses, these compounds must be of high purity. Table 2 shows the other polyols that resulted are 3% 2,3-butanediol, 2% 1,2-butanediol, 2.7% 1,3-butanediol, 2.1% 1,4-butanediol, 0.1% 1,5-pentanediol, 2.2% diethylene glycol, 2.1% triethylene glycol and 4.8% 1,2,4-butanetriol. Table 2 also shows how close these minor polyols boil to propylene glycol, ethylene glycol and glycerine. When this mixture was subjected to rectification, either at one atm. or at reduced pressure, separation to high purity compounds could not be attained.

Chueh, U.S. Pat. No. 4,057,471 used aromatic hydrocarbons as the agent in azeotropic separation of ethylene glycol and propylene glycol from carboxylic esters. He did not separate one glycol from another glycol. Becker, U.S. Pat. No. 4,021,311 used 1,2,3-trimethyl benzene as the azeotropic agent to separate propylene glycol from carboxylic esters.

OBJECTIVE OF THE INVENTION

The objective of this invention is to provide a process or method of azeotropic distillation that will enhance the relative volatility of ethylene glycol from close boiling butanediols in their separation in a rectification column. It is a further object of this invention to identify organic compounds which in addition to the above constraints, are stable, can be separated from the glycols being purified and can be recycled to the azeotropic distillation and re-used with little decomposition.

SUMMARY OF THE INVENTION

The objects of this invention are provided by a process for separating ethylene glycol from butanediol isomers which entails the use of certain organic compounds in an azeotropic distillation process.

DETAILED DESCRIPTION OF THE INVENTION

I have discovered that certain organic compounds will effectively enhance the relative volatility in azeotropic distillation of ethylene glycol from 1,2-butanediol and 1,3-butanediol when they occur as a close boiling mixture. In the mixture of polyols shown in Table 2, the major products are ethylene glycol, propylene glycol and glycerine. To be of commercial value, these compounds must be obtained in high purity.

Table 3 lists the hydrocarbons ethylbenzene, p-xylene, m-xylene, o-xylene, cumene and mesitylene which are effective azeotrope forming agents to separate ethylene glycol from 1,2-butanediol and 1,3-butanediol. They have the advantage of forming a two phase overhead product which enables separation of the ethylene glycol from the hydrocarbons by simple decantation.

The data in Table 3 was obtained in a 30 theoretical plate packed rectification column. It lists the time run at total reflux, the overhead temperature in Celcius degrees, the overhead composition at the end of the reflux period, the weight percent of ethylene glycol in the azeotrope and the relative volatility of ethylene glycol to 1,2-butanediol and 1,3-butanediol with each agent.

carbons o-xylene, m-xylene, p-xylene, ethylbenzene, cumene and mesitylene. Diisobutyl ketone was also investigated in the rectification column. Each agent was evaluated using the binary mixture of 1,2-butanediol and ethylene glycol and the ternary containing 1,2-butanediol, ethylene glycol and 1,3-butanediol. The results indicate that the separation of ethylene glycol from mixtures containing both 1,2-butanediol and 1,3-butanediol is just as good as with 1,2-butanediol and ethylene glycol.

WORKING EXAMPLES

EXAMPLE 1

Thirty grams of ethylene glycol, 20 grams of 1,2-butanediol, 10 grams of 1,3-butanediol and 40 grams of 3-heptanone were charged to a vapor-liquid equilibrium still and refluxed for five hours. The vapor composition was 94.4% ethylene glycol, 0.5% 1,2-butanediol and 5.1% 1,3-butanediol. The liquid composition was 44.4% ethylene glycol, 34.4% 1,2-butanediol and 21.2% 1,3-butanediol. This is a relative volatility of ethylene glycol to 1,2-butanediol of 1.47 and of ethylene glycol to 1,3-butanediol of 8.8.

EXAMPLE 2

A four foot rectification column packed with stainless

TABLE 3

Effective Agents For Separating Ethylene Glycol From 1,2-Butanediol and 1,3-Butanediol In Vapor-Liquid Equilibrium Still

| Agent | Azeo. Temp. | Press. mm Hg | Overhead % EG | Overhead %1,2 Bu | Overhead %1,3 Bu | Bottoms % EG | Bottoms %1,2 Bu | Bottoms %1,3 Bu | Relative Volatility EG:1,2 Bu | Relative Volatility EG:1,3 Bu |
|---|---|---|---|---|---|---|---|---|---|---|
| 3-Heptanone | 108 | 60 | 99.9 | 0.1 | — | 59.7 | 40.3 | — | 10+ | |
| 3-Heptanone | 112 | 60 | 94.9 | 0 | 5.1 | 44.4 | 34.4 | 21.2 | 10+ | 8.9 |
| Cyclohexanone | 117 | 60 | 100 | 0 | — | 56.4 | 43.6 | — | 10+ | |
| Cyclohexanone | 80 | 50 | 70.7 | 13.9 | 15.4 | 54.3 | 32.3 | 13.4 | 3.0 | 1.1 |
| Diisobutylketone | 124 | 60 | 100 | 0 | — | 62 | 38 | — | 1.27 | |
| Diisobutylketone | 125 | 60 | 95.9 | 0 | 4.1 | 50.7 | 34.0 | 15.3 | 1.71 | 1.26 |
| Methyl isoamylketone | 113 | 60 | 99.9 | 0.1 | — | 66.1 | 33.9 | — | 10+ | |
| Methyl isoamylketone | 118 | 60 | 94.3 | 0 | 5.7 | 46.7 | 27.1 | 26.2 | 10+ | 9.3 |
| Isobutyl heptylketone | 131 | 60 | 73.6 | 26.3 | — | 21.6 | 78.4 | — | 10+ | |
| Isobutyl heptylketone | 140 | 60 | 67.4 | 20.1 | 12.5 | 60.8 | 26.8 | 12.4 | 1.5 | 1.1 |
| 2,6-diMe-4-heptanone | 134 | 60 | 99.9 | 0.1 | — | 71.2 | 28.8 | — | 10+ | |
| 2,6-diMe-4-heptanone | 134 | 60 | 93.7 | 0.1 | 6.3 | 50.4 | 25.0 | 24.6 | 10+ | 7.3 |
| 2-Methoxyethyl ether | 130 | 60 | 99.9 | 0.1 | — | 71.7 | 28.3 | — | 10+ | |
| 2-Methoxyethyl ether | 132 | 60 | 99.8 | 0.1 | 0.1 | 60.8 | 21.7 | 17.5 | 10+ | 10+ |

TABLE 4

Effective Agents For Separating Ethylene Glycol From 1,2-Butanediol And 1,3-Butanediol In Rectification Column

| Agent | % EG Over. | Azeo. Temp. | Time hrs. | Overhead % EG | Overhead %1,2 Bu | Overhead %1,3 Bu | Bottoms % EG | Bottoms %1,2 Bu | Bottoms %1,3 Bu | Relative Volatility EG:1,2 Bu | Relative Volatility EG:1,3 Bu |
|---|---|---|---|---|---|---|---|---|---|---|---|
| o-Xylene | 22 | 131 | 2.5 | 85.9 | 14.1 | — | 53.3 | 46.7 | — | 1.06 | |
| o-Xylene | 9 | 130 | 5 | 92 | 8 | 0 | 41.2 | 37.6 | 21.2 | 1.1 | 10+ |
| m-Xylene | 10 | 130 | 6 | 95.3 | 4.7 | — | 49.9 | 50.1 | — | 1.11 | |
| m-Xylene | 22 | 130 | 4 | 95.2 | 4.8 | 0 | 44.6 | 34.6 | 20.8 | 1.11 | 10+ |
| p-Xylene | 10 | 130 | 5 | 98.4 | 1.6 | — | 48.1 | 51.9 | — | 1.15 | |
| p-Xylene | 8 | 130 | 9 | 94.8 | 5.2 | 0 | 48.5 | 33.4 | 21.1 | 1.11 | 10+ |
| Ethylbenzene | 7 | 121 | 5 | 99.9 | 0.1 | — | 42.3 | 57.7 | — | 1.27 | |
| Ethylbenzene | 15 | 125 | 6 | 99.9 | 0.1 | 0 | 43.3 | 35.4 | 21.3 | 1.27 | 10+ |
| Cumene | 20 | 114 | 5 | 99.9 | 0.1 | — | 61.6 | 38.4 | — | 1.26 | |
| Cumene | 10 | 120 | 8 | 99.3 | 0.7 | 0 | 48.6 | 21.6 | 29.8 | 1.18 | 10+ |
| Mesitylene | 20 | 126 | 5 | 99.1 | 0.9 | — | 48.3 | 51.7 | — | 1.17 | |
| Mesitylene | 10 | 129 | 8 | 98 | 2 | 0 | 49.8 | 18.2 | 32.0 | 1.15 | 10+ |
| Diisobutylketone | 15 | 153 | 12 | 99.8 | 0.1 | 0.1 | 32.2 | 49.2 | 18.6 | 1.31 | 1.26 |
| Diisobutylketone | 13 | 151 | 11 | 99.9 | 0.1 | — | 41.9 | 58.1 | — | 1.27 | |

Table 4 lists a number of effective agents whose relative volatilities were obtained in a 30 plate rectification column at 640 mm. Hg pressure. The temperature of the azeotrope is listed as well as the overhead and bottoms composition and the percent of ethylene glycol in the overhead. The effective agents are the aromatic hydrosteel helices was calibrated with m-xylene and p-xylene which possesses a relative volatility of 1.11 and found to have thirty theoretical plates. A solution comprising 50 grams of ethylene glycol, 40 grams of 1,2-butanediol, 20 grams of 1,3-butanediol and 100 grams of ethylbenzene was placed in the stillpot and heated. After six hours of refluxing at total reflux, the overhead composition was 99.9% ethylene glycol, 0.1% 1,2-butanediol, 0% 1,3-butanediol and the bottoms composition was 43.3% ethylene glycol, 35.4% 1,2-butanediol and 21.3% 1,3-butanediol. This gives a relative volatility of ethylene glycol to 1,2-butanediol of 1.27 and of ethylene glycol to 1,3-butanediol of 10+. These data are shown in Table 4.

I claim:

1. A method for recovering ethylene glycol from a mixture of ethylene glycol, 1,2-butanediol and 1,3-butanediol which comprises distilling a mixture of ethylene glycol, 1,2-butanediol and 1,3-butanediol in a rectification column in the presence of an azeotrope forming agent, recovering the ethylene glycol and the azeotrope forming agent as overhead product, obtaining the 1,2-butanediol and the 1,3-butanediol from the stillpot, wherein said azeotrope forming agent is one material selected from the group consisting of cyclohexanone, 3-heptanone, diisobutyl ketone, methyl isoamyl ketone, isobutyl heptyl ketone, 2,6-dimethyl-4-heptanone and 2-methoxyethyl ether.

2. A method for recovering ethylene glycol from a mixture of ethylene glycol, 1,2-butanediol and 1,3-butanediol which comprises distilling a mixture of ethylene glycol, 1,2-butanediol and 1,3-butanediol in a rectification column in the presence of an azeotrope forming agent, recovering the ethylene glycol and the azeotrope forming agent as overhead product, said overhead product forming two liquid layers, separating the ethylene glycol from the azeotrope forming agent by decantation of the two liquid layers, obtaining the 1,2-butanediol and the 1,3-butanediol from the stillpot, wherein said azeotrope forming agent is one material selected from the group consisting of o-xylene, m-xylene, p-xylene, ethylbenzene, cumene and mesitylene.

* * * * *